United States Patent [19]

Allcock et al.

[11] Patent Number: 4,880,622

[45] Date of Patent: Nov. 14, 1989

[54] WATER-SOLUBLE PHOSPHAZENE POLYMERS HAVING PHARMACOLOGICAL APPLICATIONS

[75] Inventors: Harry R. Allcock, State College, Pa.; Paul E. Austin, Williamstown, W. Va.; Sukky Kwon, University Park, Pa.

[73] Assignee: Research Corporation Technologies, Inc., Tucson, Ariz.

[21] Appl. No.: 865,504

[22] Filed: May 20, 1986

[51] Int. Cl.$^4$ .................... A61K 31/74; A01N 25/26
[52] U.S. Cl. ....................................... 424/78; 424/468
[58] Field of Search ................................ 424/78, 468

[56] References Cited

U.S. PATENT DOCUMENTS

| | | | |
|---|---|---|---|
| 4,440,921 | 4/1984 | Allcock et al. | 528/168 |
| 4,495,174 | 6/1985 | Allcock et al. | 424/78 |
| 4,801,359 | 1/1989 | Jeanne et al. | 521/27 |

OTHER PUBLICATIONS

Chem. Abstracts, vol. 102, entry 32116h, DeVissa et al., 1985.
Dissertation Abstracts Int. B. 1984, 45(1), 214–15, Order No. DA8409013.
Allcock, "Polyphosphazenes, and the Inorganic Approach to Polymer Chemistry", Sci, Prog. Oxf. 66, 355–369 (1980).

*Primary Examiner*—Joseph L. Schofer
*Assistant Examiner*—Peter F. Kulkosky
*Attorney, Agent, or Firm*—Scully, Scott, Murphy & Presser

[57] ABSTRACT

Novel poly(organophosphazene) polymers are used for the controlled release of pharmaceuticals, pesticides, herbicides, plant growth regulators and fertilizers. These polymers also act as foam control agents.

6 Claims, No Drawings

WATER-SOLUBLE PHOSPHAZENE POLYMERS HAVING PHARMACOLOGICAL APPLICATIONS

DESCRIPTION

1. Technical Field

The present invention relates to the synthesis of new macromolecules comprising water-soluble polymers known as poly(loweralkoxy loweralkoxide) phosphazenes which are biomedically-stable and surface-active for the controlled release of pharmaceuticals, pesticides, herbicides, plant growth regulators and fertilizers. These polymers also act as foam control agents.

2. Prior Art

Polyphosphazenes are synthesized as set forth by Allcock, Sci. Prog. Oxf., (1980) 66, 355–369. In one method, these polymers are prepared by the reaction of phosphorus pentachloride with ammonium chloride to yield hexachlorocyclotriphosphazene which is subsequently polymerized to form poly(dichlorophosphazene). The reaction of the chlorine groups on the polymer chain with either an alkali metal adduct of an organo hydroxy compound; a monoamine or a diamine as well as organometallic reagents is also described. The synthesis of the fluoride analog of these compounds and the subsequent reaction of the fluoride analog is also described by Evans and Allcock, J. Macromol. Sci.-Chem.L, 1981, A16, 409 and the various references cited in each of the aforementioned articles. All of the foregoing references as well as the references cited therein are incorporated by reference herein.

SUMMARY OF THE INVENTION

Considerable interest exists in the use of synthetic macromolecules as vehicles for the controlled release of chemotherapeutic agents. These macromolecules or polymeric materials swell slowly or dissolve in the gastrointestinal tract or are employed in other ways as described by Paul et al., Controlled Release Polymeric Formulations, ACS Symposium Series 33, (1976).

Generally, the area of controlled release technology includes not only the foregoing application of releasing materials into the gastrointestinal tract but also a wide variety of other medically related applications as well as non-medical applications such as pest control.

Some of the medical applications include contraception, fertility control, the delivery of narcotic antagonists, fluoride release for dental purposes and drugs to combat cancer and cardiac arrythmia or for the control of glaucoma. Non-medical applications include using the controlled release polymeric formulations for the control of pests such as snails, weeds, marine fouling organisms and the control of insect populations through the release of toxic materials or pheromones. In the area of agricultural application, these controlled release polymeric formulations have been applied for the release of fertilizers, pesticides and plant growth regulators.

A great deal of interest, is focused on the use of synthetic macromolecules in human biological applications because of the need for relatively safe macromolecules in controlled release polymeric formulations for pharmacological applications. Additionally, there is considerable interest in the use of water-soluble synthetic macromolecules with water surface tension modifying properties as foam control agents in medicinal formulations and microorgainsm synthesis of penicillins and cephalosporins. Relatively few conventional polymers are suitable in this latter regard because they fail to meet the need or biocompatability and side group stability.

The development of foams in some manufacturing processes is undesirable such as in the manufacture of other biological materials (e.g., tetracycline, aureomyicin etc.) or food stuffs by fermentation methods. Anti-foam agents are used in many of these processes in addition to paint, paper and anti-freeze manufacturing as well as in boiler water treatment, water purification and food processing. Anti-foam agents that are compatible with these processes and compositions and which are also stable must be used.

It is, therefore, an object of the present invention to overcome these and other difficulties encountered in the prior art as well as to achieve the various objectives of the prior art as set forth above.

It is a further object of this invention to provide a novel water-soluble polymer for the foregoing pharmacological and foam control applications.

It is a further object of the present invention to provide such polymers in controlled release polymeric formulations.

It is an additional object of the invention to provide such water-soluble polymers for a pharmacological compound or composition in controlled release polymeric formulations.

It is also an object of the present invention to provide novel water-soluble polymers in pesticide, herbicide, plant growth regulator and fertilizer applications, and the like.

It is a further object of the present invention to provide such water-soluble polymers for pesticides, herbicides, plant growth regulators and fertilizers in a controlled release polymeric formulation.

These and other objects have been achieved according to the present invention which provides a novel water-soluble poly(organophosphazene) polymer which may be utilized as a water-soluble polymer in pharmacological, applications, in a controlled release polymeric formulation or as a foam control agent.

DETAILED DESCRIPTION OF THE PREFERRED EMBODIMENT OF THE INVENTION

The polymers employed according to the present invention comprise a compound of the formula:

$$[NP(R)_2]_n \qquad (1)$$

(a) where R comprises a polar organic moiety
(b) n is from about 10 to about 20,000
In one embodiment, the polymer comprises
$[NP(R)_2]_n$ (a) where R is a polar organic moiety such as a short-chain polyether moiety.
(b) n is about 15,000.

The polar organic moiety may comprise an ether, polyether or higher polyethers (defined hereinafter). Other polar organic moieties include imines and polyimines, sulfides and polysulfides, esters and polyesters. The preparation of polyphosphazenes containing these and other polar organic moieties are described by Allcock, Sci. Prog. Oxf., (1980) 66, 355–369 which is incorporated herein by reference including the various citations of references set forth therein. Various mixtures of the foregoing polar organic moieties may also be employed in combination with one another as substituents along the polyphosphazene chain.

The polar organic ether moiety comprises a single lower alkoxy group or a polyether, i.e., repeating loweralkoxy groups of 2 to about 5 carbon atoms and the various isomers thereof (e.g., isopropoxy, isobutoxy, t-butoxy, isoamyloxy, t-amyloxy and the like).

The aforementioned polyethers have a molecular weight range of from about 64 to about 1000 and may contain repeating units of $CH_2O$, $C_3H_7O$, $C_2H_4O$, $C_3H_6O$, $C_4H_8O$ or mixtures thereof. The terminal group of this polyether chain may be a single alkyl group such as $CH_3$, $C_2H_5$, $C_3H_7$, C or an aryl group such as $C_6H_5$ as well as mixtures thereof.

In one embodiment, R may be

 (1)

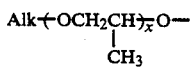 (2)

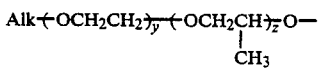 (3)

where x is from 1 to about 21, Alk is lower alkyl and where the sum of y and z is from 2 to about 100.

In the foregoing, lower alkyl comprises an alkyl group having from 1 to about 5 and especially from 1 to about 3 carbon atoms.

The polar organic moiety preferably includes those groups comprising mono-loweralkoxy, the di-loweralkoxy or tri-loweralkoxy groups or mixtures thereof and preferably are ethoxy, diethoxy or triethoxy groups or mixtures thereof attached to the polyphosphazene chain or backbone whereas the preferred terminal loweralkyl group attached to the ethoxy, diethoxy or triethoxy groups comprises a methyl group.

Mixtures of ether repeating units on the polymer chain or backbone may be employed by which it is intended to include a single unit or alternating repeating units of an ethylene oxide group and the like linked to a propylene oxide or butylene oxide group to form chains some of which may be terminated with a methyl group others of which may be terminated with an ethyl group and the like all on the same polyphosphazene molecule or on different polyphosphazene molecules.

The polymers of the present invention have a glass transition temperature from about $-100°$ C. to about $20°$ C.

The foregoing polymers may be dissolved and/or suspended in water or any other suitable liquid medium in which the polymers are soluble and/or dispersible and combined with a pharmacological compound or composition (i.e., pharmaceuticals), pesticide, herbicide, plant growth regulator or fertilizer to form a composition of matter so that when the composition is dry, the polymer will act as a matrix for the pharmaceutical, pesticide, herbicide, plant growth regulator or fertilizer to thereby provide an article of manufacture for the controlled release of such agents. The various methods of manufacture and applications of controlled release polymeric formulations are described by Paul and Harris, *Controlled Release Polymeric Formulations*, (supra) which is incorporated by reference herein. The various pharmaceuticals, pesticides, herbicides, plant growth regulators and fertilizers that may be employed in this respect are disclosed therein and incorporated herein by reference.

Additionally, the various pharmacological compounds or compositions (i.e., pharmaceuticals) that may be employed in the article of manufacture of the present invention are listed in the *Physicians' Desk Reference*, (1983) which is incorporated herein by reference and include allergens, amebicides and trichomonacides, amino acid preparations, analeptic agents, analgesics, analgesics/antacids, anesthetics, anorexics, antacids, anthelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis, antifibrinolytic agents, antifrbrotics (systemic), antiflatulents and combinations, antifungal agents, antigonadotropin, antihistamines, antihyperammonia agents, anti-inflammatory agents, antimalarials, antimetabolites, anti-migraine preparations, antinauseants, antineoplastics, anti-obesity preparations, antiparasitics, anti-parkinsonism drugs, antipruritics, antipyretics, antispasmodics and antichloinergics, antioxoplasmosis agents, antitussives, antivertigo agents, antiviral agents, biologicals, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, contraceptives (oral and topical), cough and cold preparations, decongestants, expectorants and combinations, diuretics, emetics, enzymes and digestants, fertility agents, fluorine preparations, glactokinetic agents, geriatrics, germicides, hematinics, hemorrhodial preparations, histamine H., receptor antagonists, hormones, hydrocholeretics, hyperblycemic agents, hypnotics, immunosuppressives, laxatives, mucolytics, muscle relaxants, narcotic antagonists, narcotic detoxification agents, opthalmologicals, osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics and combinations, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the *Physicians' Desk Reference*, (supra).

The polymers of the present invention are used in an amount sufficient to form a matrix around the composition or material to be released in the time release formulations or to act as a carrier for such compositions or materials in such formulations and can be employed in an amount sufficient to permit the delayed time release of a composition or material into its environment, e.g., anywhere from about 1% by weight to about 99% by weight of the time release formulation and especially from about 5% by weight to about 99% by weight of the time release formulation.

The polymers of the present invention are also used as anti-foaming agents in fluid compositions especially in aqueous fluid compositions above the specific cloud point or reversible solubility temperature of these polymers and may be employed in a foam controlling amount, e.g., amounts as low as about 2 ppm to about 10% by weight of the composition, especially from about 25 ppm to about 5% by weight of the composition.

The polymers of the present invention are also used as emulsifying agents in fluid compositions especially in oil in water compositions and may be employed as emulsifying agents in an amount as low as about 2% to about 20% by weight of the compositions. These polymers are typically found at the oil/water interface and act similarly to those of the organic class of emulsifiers such as Span TM, MYRJ TM, and TWEENS TM. Both water in oil and oil in water type emulsions may be formed using the polymers of the invention. Both types of emulsions are obtained by methods well known in the art. Cosmetic and medicinal lotions, ointments or creams are prepared according to the present invention as well as emulsions of monomers in water for the formation of latexes such as styrene, styrene butadiene, acrylic ester and vinyl ester latexes known in the art. The components of and methods of formation of emulsions and their application is more fully discussed in *Kirk-Othmer, Encyclopedia of Chemical Technology*, 3rd Ed., Vol 8, pp. 900–930, including the various references cited therein, all of which is incorporated herein by reference. Briefly, the emulsions of the present invention are formed by combining the so-called water phase with the so-called oil phase and the polymer of the present invention and mixing them until an emulsion is obtained. The amount of the oil-phase and water-phase components and polymer will vary depending on whether an oil in water or water in oil emulsion is to be produced and is easily determined by a person having ordinary skill in the art. The oil phase and the water phase are made up of water components and oil components which are the components per se or components that may have other materials dissolved in them. For example, the oil phase of a cosmetic lotion made according to the present invention may be a combination of a mineral oil and a scented oil. Similar combinations are well known and readily understood by a person having ordinary skill in the emulsion art.

The amount of polymer employed in either the time release formulation or foam control processes or as emulsifying agents can be readily and easily determined by a person having ordinary skill in the art.

In one embodiment of the invention, the polyphosphazene polymers (I) are cross-linked and then employed as a time-release matrix as described herein. Cross-linking may be effected by irradiating the polyphosphazene polymers with gamma radiation, ultraviolet radiation, x-ray radiation or any radiation that will generate free radicals in the polyphosphazene polymers.

The cross-linking is proportional to the amount of radiation to which the polyphosphazene polymers are exposed, either in terms of intensity of radiation, time of radiation or both, all of which is well known in the art.

In addition to cross-linking the polymers by irradiation, the polyphosphazene polymers may also be chemically cross-linked either with diols, diamines and the like, as well as the chemical incorporation of unsaturated side groups on the polyphosphazene polymer backbone, such unsaturated groups being capable of further polymerization in the presence of a free radical initiator such as by irradiation or peroxides, e.g., benzoyl peroxide and the art-known equivalents thereof.

The diols and the diamines may be incorporated into the polyphosphazene polymer as a salt of the diol or diamine such as the salts based on Group IA or Group IIA metals of the Periodic Table of the Elements, the sodium and potassium salts being especially useful in this regard because of their availability. The salts of the diols and diamines in this regard comprise those salts in which both hydroxy groups of the diols and both amino groups of the diamines are reacted to form a salt of the aforementioned metals. Thus, for example, the disodium salt of the diols or the disodium salts of the diamines are employed in this respect.

Some of the diols that may be employed comprise alkylene glycols having from 2 to about 5 carbon atoms (e.g., 1,4-butane diol, neopentylglycol and the like), poly(alkyleneoxy) glycols having from about 3 to about 15 carbon atoms and the like. Aromatic diols may also be employed in this respect such as hydroquinone, resorcinol, bis-phenol-A, bis-phenol-F and the like. The disodium salts of these compounds would be employed in this respect such as the disodium salt of hydroquinone, resorcinol and the like.

Diamines that may be employed in this regard comprise the alkylene diamines having from about 2 to about 5 carbon atoms or cyclic amines such as the diamino benzenes or toluenes and heterocyclic amines such as piperazine, imidazolidine, pyrazolidine and pyrazoline.

Chemical cross-linking may also be effected by reacting the polyphosphazene polymers with trifunctional or other polyfunctional hydroxy or amine compounds such as pentaerythritol, phloroglucinol, pyrogallol and the like. The aliphatic triamines or polyamines as known in the art may also be employed in this respect as well such as the triamino alkanes having from about 3 to about 6 carbon atoms and the triamino monocyclic aromatic or cyclic compounds. When the trifunctional or polyfunctional hydroxy or amine compounds are employed, they tend to promote 3-dimensional cross-linking.

The unsaturated groups that are introduced into the polyphosphazene polymer which may be subsequently polymerized by means of a free radical polymerization mechanism may comprise compounds having allyl groups and the like such as allyl amine or allyl alcohol. The polyphosphazene polymers are chemically cross-linked by the addition of the aforementioned chemical cross-linking agents to poly(dichlorophosphazene) in which the chemical cross-linking components comprise anywhere from up to about 30% (on an equivalent basis) of the polar organic moiety (as defined herein) that is introduced into the poly(dichlorophosphazene) polymer. The chemical cross-linking agents may be added at the same time as the polar organic moieties (referred to as co-substitution), or before or after the polar organic moieties are reacted with the poly(dichlorophosphazene). The co-substitution reaction is preferred.

The chemical cross-linking agents such as the diols and the diamines will produce the cross-linking immediately upon reaction with the poly(dichlorophosphazene) whereas the unsaturated substituents such as the allyl amino or allyl oxy substituents can be subsequently reacted in the presence of a free radical initiator (e.g., benzoyl peroxide) to effect cross-linking.

The polyphosphazene polymers (I) are cross-linked by irradiation after the poly(dichlorophosphazene) is substituted with the polar organic moieties (as defined herein) or after the poly(dichlorophosphazene) has the various aforementioned chemical cross-linking compounds introduced into it.

The polymers are cross-linked to a degree sufficient to allow them to function as a time-release matrix as described herein.

EXAMPLE I

Poly(dichlorophosphazene) having a molecular weight of about 15,000 was prepared by conventional methods disclosed in detail by Allcock et al. (1965), *J. M. Chem. Soc.*, 87, 4216; Allcock et al. (1966), *Inorg. Chem.*, 5, 1709; Allcock et al. (1964), *Can. J. Chem.*, 42, 447 and Allcock et al. (1975), *Macromolecules*, 8, 36; all of which are incorporate herein by reference.

EXAMPLE II

Synthesis of $[NP(OCH_2CH_2OCH_3)_2]_n$

Poly(dichlorophosphazene) (186 g, 1.6 mol) as described in Example I was dissolved in dry tetrahydrofuran (4L) under a dry nitrogen atmosphere. The dissolved polymeric solution was added dropwise to the sodium salt of 2-methoxyethanol prepared from 2-methoxyethanol (475 mL, 6.02 mol) and sodium metal (113 g, 4.91 mol) in tetrahydrofuran (2L) and tetrabutylammonium bromide (3 g). This solution was stirred at reflux temperature for three days under a dry nitrogen atmosphere. The polymeric solution was slowly poured into heptane (7 gal) and the polymer precipitated from solution and was collected by suction filtration. The polymer was dissolved in water and was dialyzed against water to remove occluded salts. Removal of the water yielded 210 g of a clear film-forming elastomeric material. This was dried over $P_2O_5$ in vacuo.

EXAMPLE III

Synthesis of $[NP(OCH_2CH_2OCH_2CH_2OCH_3)_2]_n$

Poly(dichlorophosphazene) (128 g, 1.10 moles) as described in Example I was dissolved in dry tetrahydrofuran (4L) under a dry nitrogen atmosphere with vigorous agitation. The dissolved polymeric solution was added dropwise to the sodium salt of 2-(2-methoxyethoxy)ethanol prepared from sodium metal (76 g, 3.3 mol) and 2-(2-methoxyethoxy)ethanol (500 ml, 3.8 mol) in tetrahydrofuran (2L) and tetrabutylammonium bromide (3 g). This solution was stirred at reflux for three days under a dry nitrogen atmosphere. The polymeric solution was slowly poured into heptane (7 gal) and the polymer precipitated from solution and was collected by suction filtration. The polymer was dissolved in water and was dialyzed against water to remove occluded salts. Removal of the water yielded 140 g of a clear, elastomeric, film-forming material. This was dried over $P_2O_5$ in vacuo.

Proton decoupled $31_P$ NMR spectra were obtained for the polymers of Examples II and III in the FT mode at 40.5 MHz using a JEOL JNM-PS-100 spectrometer equipped with a Nicolet 1080 data processing system. Infrared spectra were obtained with the use of a Perkin Elmer 580 spectrometer. Polymer separations and molecular weight approximations were obtained by gel permeation chromatography with the use of a Waters Associates ALC-201 instrument. The column arrangement was a 4 ft.×⅜ in. $10^5$ styragel column for use with tetrahydrofuran solvent at a flow rate of 2.4 mL/min.

The products obtained according to Examples II and III above were characterized by a combination of $^{31}P$ NMR, $^1H$ NMR, infrared spectroscopy, HLB (Hydrophile-Lipophile Balance), and elemental microanalysis (see Table I). The $^{31}P$ NMR spectra were sharp singlets for species III at −5.41 ppm and species IV at −7.68 ppm. The $^1$NMR spectra were consistent with the structures postulated. Infrared spectra showed evidence of the —P═N— backbone in the 1100–1300 cm$^{-1}$ range. Aliphatic C—H bonds were detected from peaks in the 2900–3000 cm$^{-1}$ region. The HLB for the polymer of Example II was calculated to be 15.38 and for the polymer of Example III was calculated to be 16.81.

TABLE I

| Compound | NMR Singlets p.p.m. | Molecular Weight Mn | % Yield | HLB |
| --- | --- | --- | --- | --- |
| $[NP(OCH_2CH_2OCH_3)_2]_n$ | −5.41 | 1 × 10$^6$ | 76.9% | 15.38 |
| $[NP(OCH_2CH_2OCH_2CH_2OCH_3)_2]_n$ | −7.68 | 1 × 10$^6$ | 84.09% | 16.81 |

Starting materials that may be used in lieu of the 2-methoxy ethanol or 2(2-methoxyethoxy) ethanol of Examples II and III comprise 1-methoxy-2-propanol; 3-methoxy-2-butanol;

  (A)

  (B)

where x can be from 1 to about 100

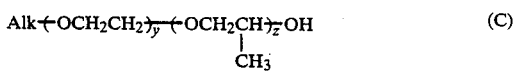  (C)

where the sum of y and z can be from 2 to about 100, and Alk is a lower alkyl, especially an alkyl group having from 1 to about 5 carbon atoms or from 1 to about 3 carbon atoms.

The foregoing compounds (A), (B) and (C) comprise adducts, polymers and copolymers of ethylene and propylene oxide and are known in the art. The molecular weight is selected so that the compounds are readily miscible with the phosphazene polymer or are soluble in a solvent common to both the phosphazene polymer and the compound. The manufacture of these compounds is disclosed and readily discernible in British Patent No. 1,418,526; U.S. Pat. Nos. 3,456,013; 3,956,401; 3,830,267; 4,151,269; 4,060,501; 3,892,522; 3,927,104 and *Encyclopedia of Chemical Technology*, 3rd Ed., all of which are incorporated herein by reference.

EXAMPLE IV

Drug Delivery From Methoxyethoxyethoxyphosphazene Hydrogel

Poly[bis(methyoxyethoxyethyoxy)phosphazene] (8 g, 0.029 mol) (1) was dissolved in 30 mL of deionized water. The viscous polymer solution was poured into a Petri dish (ID: 6 cm). Water was slowly removed by placing the Petri dish in a glove box with a slow flow of dry air. After 7 days, a dry and uniform film of polymer (1) was obtained. The Petri dish was sealed and exposed to $^{60}$Co γ-ray radiation for 7 h to obtain an irradiated film of polymer (1) which was allowed to swell in water and thereby produce a hydrogel polymer film (2). A cork borer (ID: 2 cm) was used to cut a round disk (thickness: 0.8 cm) in film (2) which was transparent and uniform and had good mechanical strength.

Film (2) was immersed in a drug solution comprising tripelennamine hydrochloride (5 g/100 mL of water). After 1 day, film (2) was transferred to another tripelennamine hydrochloride solution (5 g/100 mL). Film (2) formed a loaded hydrogel by allowing it to equilibrate in the drug solution for a sufficient time to ensure that no significant concentration gradient existed through film (2). The loaded hydrogel was washed with deionized water before it was transferred to pure water (100 mL) and was placed in a new water sample (100 mL) every hour. All drug release experiments were conducted at 37° C. in a temperature-controlled water bath.

The linearity between the concentration of tripelennamine hydrochloride and the absorbance at 306 nm in UV spectrum was obtained by the Lambert-Beer law. The amount of released tripelennamine hydrochloride was calculated based on this standard line of tripelennamine hydrochloride. It was found that the loaded hydrogel contained approximately 87 mg of tripelennamine hydrochloride by weighing it after drying under vacuum. After the first hour, 58 mg of tripelennamine hydrochloride was released from the loaded hydrogel while during the second hour, 17 mg of drug was released. The amount of tripelennamine hydrochloride released in the succeeding hours decreased significantly (after 3 h: 8 mg; after 4 h: 3 mg; after 5 h: 0.7 mg; after 6 h: 0.2 mg; and after 7 h: 0.1 mg), until at 8 h virtually all of the loaded drug diffused out of film (2).

EXAMPLE V

Antifoaming Efficiency/Aqueous Surface Modification

The antifoaming efficiency of Poly bis(methoxy ethoxyethanol)phosphazene was determined by adding with a micropipette, increments of the polymer dissolved as 1% in water to 11 liters of vigorously aerated broth liquor composition contained in a 14 liter glass measuring NBS Microfirm fermentor inoculated with E. Coli 104 at 37° C. and aerated at 5 liters/minute of air at 400 rpm agitation. The broth liquor composition consisted of an aqueous dispersion of the following ingredients:

| Yeast Extract | 10 g/l |
|---|---|
| Casein hydrolysate | 5 g/l |
| Glucose | 10 g/l |
| KH$_2$PO$_4$ | 5 g/l |
| MgSO$_4$ | 1 g/l |

The test was carried out with the composition at 37° C. Incremental addition of the polymer to the foaming liquor was continued until foaming was suppressed for a period of at least 22 hours and the total addition (as parts per million) recorded. It was found that foaming was suppressed for 22 hours with the addition of as little as 25 to 30 parts per million of the Poly bis(methoxy ethoxyethanol) phosphazene, that is [NP(OCH$_2$CH$_2$OCH$_2$OCH$_3$)$_2$]$_n$. A viable cell count at harvest was 3.3×10$^8$ cells/ml.

Although the invention has been described by reference to some embodiments, it is not intended that the novel compounds, method and article of manufacture of this invention are to be limited thereby but that modifications are intended to be included as falling within the spirit and broad scope of the foregoing disclosure and the following claims.

We claim:

1. A controlled release article of manufacture comprising a member selected from the group consisting of pharmaceuticals, pesticides, herbicides, plant growth regulators, and fertilizers in a physical admixture with a matrix of a polymer of the formula:

[NPR(R$_2$)]n wherein (a) R is selected from the group consisting of lower alkoxy ethers or polyethers, imines, polyimines, sulfides, polysulfides, esters and polyesters, and (b) n is from about 10 to about 20,000.

2. The article of claim 1 wherein R is a polyether.

3. The article of manufacture of claim 1 where R is:

Alk—OCH$_2$CH$_2$)$_x$O— x is from 1 to about 100
and Alk is lower alkyl.

4. The article of manufacture of claim 1 where R is:

$$\text{Alk}(\text{O}-\text{CH}_2\text{CH})_x\text{O}-$$
$$|$$
$$\text{CH}_3$$

x is from 1 to about 100 Alk is lower alkyl.

5. The article of manufacture of claim 1 where R is:

$$\text{Alk}(\text{OCH}_2\text{CH}_2)_y(\text{O}-\text{CH}_2\text{CH})_z\text{O}-$$
$$|$$
$$\text{CH}_3$$

the sum of y and z is from 2 to about 100 Alk is lower alkyl.

6. The article of manufacture of any of claims 1 through 5 where said polymer is cross-linked.

* * * * *

UNITED STATES PATENT AND TRADEMARK OFFICE
CERTIFICATE OF CORRECTION

PATENT NO. : 4,880,622

DATED : November 14, 1989

INVENTOR(S) : Harry R. Allcock, et al.

It is certified that error appears in the above-identified patent and that said Letters Patent is hereby corrected as shown below:

Column 3, line 13: "C" should read as --$C_4H_9$--

Column 8, line 13: "$^1$NMR" should read as --$^1$H NMR--

Signed and Sealed this

Tenth Day of September, 1991

Attest:

HARRY F. MANBECK, JR.

Attesting Officer     Commissioner of Patents and Trademarks